United States Patent
Pierce et al.

(10) Patent No.: US 11,429,591 B1
(45) Date of Patent: Aug. 30, 2022

(54) COMPONENT LINKS IN MOLECULAR DATABASES

(71) Applicant: Benchling, Inc., San Francisco, CA (US)

(72) Inventors: Alan Garrett Pierce, San Francisco, CA (US); Vineet Gopal, San Francisco, CA (US); Thomas Christiansen-Salameh, Oakland, CA (US); Karen Gu, San Francisco, CA (US)

(73) Assignee: Benchling, Inc., San Francisco, CA (US)

( * ) Notice: Subject to any disclaimer, the term of this patent is extended or adjusted under 35 U.S.C. 154(b) by 0 days.

(21) Appl. No.: 17/733,548

(22) Filed: Apr. 29, 2022

(51) Int. Cl.
*G06F 21/00* (2013.01)
*G06F 16/23* (2019.01)
*G06F 21/62* (2013.01)

(52) U.S. Cl.
CPC ...... *G06F 16/2365* (2019.01); *G06F 16/2379* (2019.01); *G06F 21/6218* (2013.01)

(58) Field of Classification Search
CPC ............. G06F 16/2365; G06F 16/2379; G06F 21/6218
See application file for complete search history.

(56) References Cited

U.S. PATENT DOCUMENTS

| | | | |
|---|---|---|---|
| 10,790,045 B1 * | 9/2020 | Goyal | G16C 20/70 |
| 11,264,140 B1 * | 3/2022 | Tai | G16H 50/20 |
| 2008/0281915 A1 * | 11/2008 | Elad | G06Q 10/10 |
| | | | 709/204 |
| 2009/0024547 A1 * | 1/2009 | Lu | G16C 20/30 |
| | | | 706/21 |
| 2018/0137239 A1 * | 5/2018 | Apte | G16B 20/00 |
| 2019/0010533 A1 * | 1/2019 | Wong | G16B 20/00 |
| 2020/0181710 A1 * | 6/2020 | Steelman | C12Q 1/6886 |
| 2020/0199555 A1 * | 6/2020 | Zhang | C12N 9/22 |

(Continued)

OTHER PUBLICATIONS assets.geneious.com [online], "Geneious "Parents and Descendents"," Mar. 4, 2015, retrieved on May 9, 2022, retrieved from URL<http://assets.geneious.com/manual/8.0/GeneiousManualse35.html>, 2 pages.

(Continued)

*Primary Examiner* — Mahfuzur Rahman
(74) *Attorney, Agent, or Firm* — Fish & Richardson P.C.

(57) ABSTRACT

Methods, systems, and apparatus, including computer programs encoded on a computer storage medium, for updating a molecular database. In one aspect, a method comprises: receiving a request to update a target molecule component stored in the molecular database; updating the data defining a target molecule represented by the target molecule component; identifying a set of target component links that reference the target molecule component; identifying, for each of the target component links, a respective validation criterion associated with the target component link; determining, for each of the target component links, a new validation status for the target component link by evaluating the validation criterion associated with the target component link; and updating the current validation status of each target component link to the new validation status for the target component link.

20 Claims, 7 Drawing Sheets

(56) References Cited

U.S. PATENT DOCUMENTS

| | | | |
|---|---|---|---|
| 2020/0286625 A1* | 9/2020 | Aliper | G16B 5/00 |
| 2022/0005552 A1* | 1/2022 | Galkin | G16H 50/30 |
| 2022/0044761 A1* | 2/2022 | O'Connell | G16B 20/20 |
| 2022/0108262 A1* | 4/2022 | Celia | G05B 19/41885 |

OTHER PUBLICATIONS

Edgar et al., "Multiple sequence alignment," Current Opinion in Structural Biology, Jun. 2006, 16(3):368-373.

Golovin et al., "Google Vizier: A Service for Black-Box Optimization," Proceedings of the 23rd ACM SIGKDD International Conference on Knowledge Discovery and Data Mining, Aug. 2017, pp. 1487-1495.

ncbi.nlm.nih.gov [online], "NCBI GenBank," Dec. 3, 1998, retrieved on May 9, 2022, retrieved from URL<https://www.ncbi.nlm.nih.gov/genbank/>, 1 page.

* cited by examiner

COMPONENT LINKS IN MOLECULAR DATABASES

BACKGROUND

This specification relates to a database for storing data defining molecules and relationships between molecules.

A molecule can refer to a group of bonded atoms. Examples of molecules include deoxyribonucleic acid (DNA) molecules, ribonucleic acid (RNA) molecules, xeno nucleic acid (XNA) molecules, protein molecules, peptide molecules, antibody molecules, drug molecules, antibody-drug conjugate molecules, carbohydrate molecules, and lipid molecules.

A database can electronically store data representing molecules and relationships between molecules, e.g., in one or more computer clusters or in cloud storage.

SUMMARY

This specification describes a molecular database management system implemented as computer programs on one or more computers in one or more locations.

The molecular database management system manages a molecular database that stores: (i) a set of molecule components (which can also be referred to as "molecule entities"), and (ii) a set of component links. Each molecule component includes data defining a respective molecule. Each component link references a respective pair of molecule components and includes a validation status that defines whether the pair of molecule components have a valid containment relationship.

Each component link can be associated with a respective validation criterion that defines a criterion for evaluating whether the pair of molecule components referenced by the component link have a valid containment relationship. For example, a validation criterion can define that a first molecule component has a valid containment relationship with a second molecule component if a molecule represented by the first molecule component is included in a molecule represented by the second molecule component.

Particular embodiments of the subject matter described in this specification can be implemented so as to realize one or more of the following advantages.

The molecular database described in this specification can efficiently represent complex networks of relationships between molecules in a set of molecules stored in the molecular database. In particular, the molecular database can represent connections between pairs of molecules using component links, where the type of relationship represented by a component link is defined by an adjustable validation criterion that is specific to the component link. Each component link includes a validation status that defines the validity of the relationship represented by the component link. The validation status of component links can adaptively toggle between "valid" and "invalid" states as the molecular data stored in the database dynamically changes.

The molecular database management system described in this specification can leverage the rich representational capacity of component links to maintain the consistency of data stored in the molecular database. In particular, the system tracks and updates the validation status of component links in the molecular database as the data stored in the molecular database changes over time, e.g., in response to user requests, and as molecular data is loaded into and removed from the database. In response to determining that the validation status of a component link has become invalid as a result of a modification to a molecule component referenced by the component link, the system can propagate the modification to the molecule component through the database to restore the consistency of the molecular data.

The system can maintain certain component links in an invalid state, e.g., because access control conditions implemented to maintain the integrity of the molecular data prevent the system from propagating certain modifications. The system can notify users regarding invalid component links, e.g., by way of a user interface, and prompt users to resolve issues preventing the component links from being restored to valid states. By allowing component links to assume invalid states, the system enables the molecular database to recover from errors and inconsistencies without discarding information (e.g., by deleting invalid connections) or compromising data integrity (e.g., by allowing modifications to propagate uncontrolled through the molecular database).

The details of one or more embodiments of the subject matter of this specification are set forth in the accompanying drawings and the description below. Other features, aspects, and advantages of the subject matter will become apparent from the description, the drawings, and the claims.

BRIEF DESCRIPTION OF THE DRAWINGS

Like reference numbers and designations in the various drawings indicate like elements.

DETAILED DESCRIPTION

Figure 1:
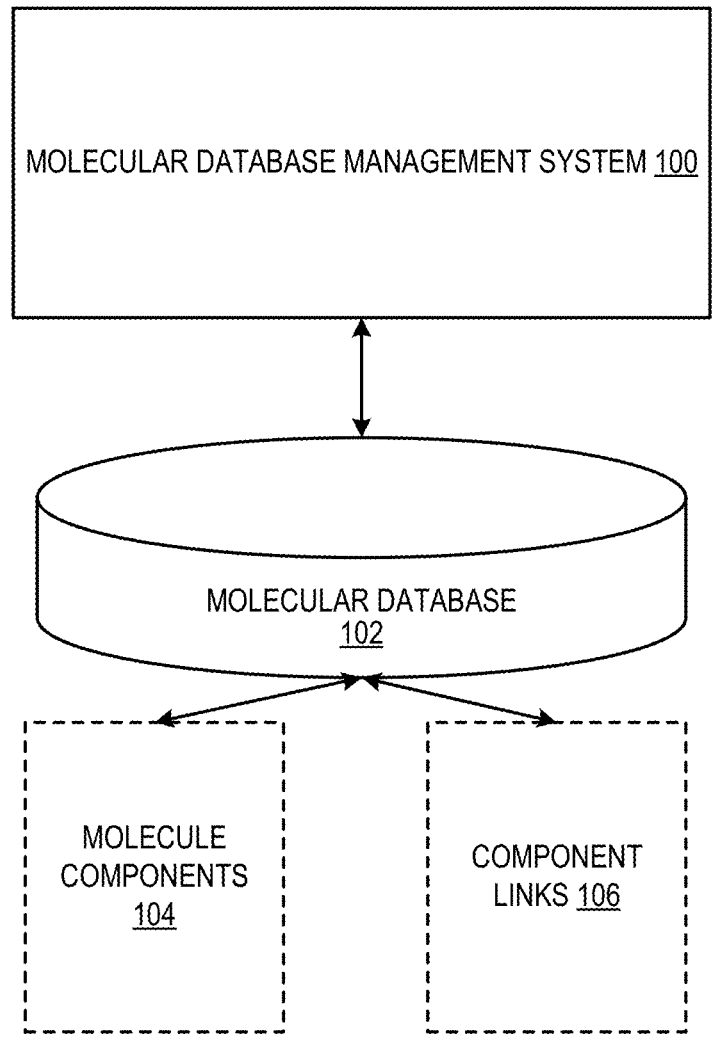
FIG. 1 shows a molecular database and a molecular database management system.

FIG. 1 shows a molecular database 102 and a molecular database management system 100.

The molecular database 102 stores data defining: (i) a set of molecule components 104, and (ii) a set of component links 106.

Each molecule component includes data defining a respective molecule. Examples of molecules include deoxyribonucleic acid (DNA) molecules, ribonucleic acid (RNA) molecules, xeno nucleic acid (XNA) molecules (or other molecules resulting from chemical modifications to DNA or RNA molecules), protein molecules, peptide molecules, antibody molecules, drug molecules, antibody-drug conjugate molecules, carbohydrate molecules, lipid molecules, and linker molecules. Throughout this specification, certain molecules may be referred to as being defined by a sequence of bases. For instance, DNA molecules and RNA molecules can be defined by sequences of nucleotide bases, and protein molecules can be defined by sequences of amino acid bases (which can also be referred to as sequences of amino acid residues or sequences of amino acids). A molecule component can represent a molecule in any appropriate format, e.g., using Hierarchical Editing Language for Macromolecules (HELM).

In some implementations, each molecule component can include version history data that defines one or more previous versions of the molecule represented by the molecule component. That is, the molecule represented by a molecule component can be modified one or more times, and each previous version of the molecule can be represented in the version history data. A molecule represented by a molecule component can be modified, e.g., by manual editing performed by a user, or by an automated procedure, as will be described in more detail below with reference to the molecular database management system 100. In some instances, the version history for a molecule component can be empty, e.g., if the molecule represented by the molecule component has not been modified since being instantiated.

In some implementations, each molecule component can include access control conditions specifying conditions that must be satisfied in order for the molecule represented by the molecule component to be modified. For example, an access control condition can specify that a molecule represented by a molecule component can be modified only if the modification is manually authorized by a user that is designated as having authorization to approve the modification. In some instances, the access control conditions can include "read" control conditions and "write" control conditions. Read control conditions can specify conditions that must be satisfied in order for a user to view the molecule component or the contents of the molecule component. Write control conditions can specify conditions that must be satisfied in order for a user the modify the contents of the molecule component.

Each component link in the molecular database 102 includes data identifying: (i) a pair of molecule components in the molecular database 102 that are referenced by the component link, and (ii) a current validation status of the component link. The current validation status of a component link defines whether the pair of molecule components referenced by the component link have a valid "containment" relationship. Generally, a containment relationship can refer to any appropriate relationship between a pair of molecule components. A few examples of validation criteria for evaluating the validity of containment relationships between pairs of molecule components are described next.

In one example, a validation criterion can define that a first molecule component representing a first molecule has a valid containment relationship with a second molecule component representing a second molecule if the first molecule is included within the second molecule. A first molecule can be referred to as being included within a second molecule if the molecular structure of the first molecule matches the molecular structure of a corresponding portion of the second molecule. For instance, a first molecule can be referred to as being included within a second molecule if a sequence of bases defining the first molecule matches a subsequence of a sequence of bases defining the second molecule.

As another example, a validation criterion can define that a first molecule component representing a first molecule has a valid containment relationship with a second molecule component representing a second molecule if a "translated" (or "transformed") version of the first molecule is included within the second molecule. More specifically, if the first molecule and the second molecule are of different types, then a "translated" version of the first molecule refers to a molecule obtained by mapping the first molecule onto a corresponding molecule of the same type as the second molecule. For instance, if the first molecule is a DNA molecule and the second molecule is a protein molecule, then the DNA molecule can be mapped onto (i.e., translated into) a corresponding protein (e.g., that a cell would synthesize by processing the DNA molecule) using a codon table. In some instances, the validation criterion can specify the translation (transformation) operation, e.g., by specifying a codon table from a set of possible codon tables.

As another example, a validation criterion can define that a first molecule component representing a first molecule has a valid containment relationship with a second molecule component representing a second molecule if a similarity measure between: (i) the first molecule, and (ii) a portion of the second molecule, satisfies a threshold. A validation criterion can measure similarity between molecules (or portions thereof) using any appropriate similarity measure. For instance, a validation criterion can measure similarity between molecules represented by respective sequences of bases using a Hamming distance, i.e., that measures a number of positions at which the sequences differ, or a Levenshtein distance. In a particular example, a similarity measure between a first molecule and a corresponding portion of a second molecule can satisfy a threshold if a sequence of bases defining the first molecule is within a predefined Hamming distance of a subsequence of a sequence of bases defining the second molecule.

As another example, a validation criterion can define that a first molecule component representing a first molecule has a valid containment relationship with a second molecule component representing a second molecule if a similarity measure between: (i) a translated version of the first molecule, and (ii) a portion of the second molecule, satisfies a threshold. For instance, the first molecule can be a DNA molecule, the second molecule can be a protein molecule, the translated version of the first molecule can be a protein molecule, and the similarity measure can be, e.g., a Hamming distance.

As another example, a validation criterion can define that a first molecule component representing a first molecule has a valid containment relationship with a second molecule component representing a second molecule if a binding affinity between the first molecule and the second molecule satisfies a threshold. For instance, a validation criterion can define that the first molecule component and the second molecule component have a valid containment relationship if the first molecule and the second molecule have at least a predefined minimum binding affinity.

As another example, each molecule component can include metadata indicating whether the molecule represented by the molecule component is "plausible," e.g., is predicted to exist in a stable state in the natural world, or is predicted to be synthesizable. In this example, a validation criterion can define that a first molecule component has a valid containment relationship with a second molecule component only if the metadata for both molecule components indicates that the corresponding molecules are plausible.

A validation criterion can characterize the validity of a containment relationship between a first molecule component representing a first molecule and a second molecule component representing a second molecule by comparing a sequence of bases defining the first molecule to a sequence of bases defining the second molecule, as described above. In some cases, a sequence of bases defining a molecule can include one or more "wildcard" (i.e., unspecified) bases, where a wildcard base is evaluated as matching any base in a corresponding position in another sequence of bases.

Generally, a validation criterion for evaluating the validity of a containment relationship between pairs of molecule components can be a "non-symmetrical" criterion or a "symmetrical" criterion. More specifically, a validation criterion can be referred to as being non-symmetrical if the validation criterion can evaluate to different values (i.e., of "valid" or "non-valid") for a pair of molecule components depending on the ordering of the molecule components. For instance, a validation criterion that evaluates whether a first molecule is included within a second molecule is non-symmetrical. A validation criterion can be referred to as being symmetrical if the validation criterion evaluates to the same value for a pair of molecule components irrespective of the ordering of the molecule components. For instance, a validation criterion that evaluates binding affinity between a first molecule and a second molecule is symmetrical.

A component link can further include containment parameters that parameterize the evaluation of the validation criterion of the component link. For example, a component link referencing a first molecule and a second molecule can include containment parameters that identify a portion of the second molecule. In this example, the component link can have a validation criterion that evaluates whether the first molecule is included within the portion of the second molecule identified by the containment parameters. Containment parameters can identify a portion of a molecule in any appropriate way. For instance, for a molecule defined by a sequence of bases, containment parameters can identify a portion of the molecule by identifying a subsequence of the sequence of bases, e.g., by identifying respective first and last indices of the subsequence in the sequence of bases. In some cases, containment parameters can identify multiple non-contiguous portions of a molecule.

Each component link in the molecular database 102 can have a respective validation criterion for evaluating whether the pair of molecule components referenced by the component link have a valid containment relationship. In particular, different component links can be associated with different validation criteria. In some cases, a single pair of molecule components can be referenced by multiple component links, each of which have respective containment parameters, validation criteria, or both. As such, component links can characterize respective containment relationships between a single pair of molecule components along multiple "dimensions," i.e., where each dimension corresponds to a respective component link. Moreover, a set of component links referencing a single pair of molecule components can include one or more component links with "valid" validation statuses and one or more component links with "invalid" validation statuses.

The molecular database 102 can include any appropriate number of molecule components 104 and any appropriate number of component links 106. For example, the molecular database 102 can include thousands, tens of thousands, or hundreds of thousands of molecule components 104 and component links 106. Moreover, the molecular database 102 can store molecule components representing multiple types of molecules. For example, the molecular database 102 can simultaneously store one or more molecule components representing DNA molecules and one or more molecule components representing protein molecules.

The molecular database management system 100 enables users to interact with the molecular database 102, e.g., by loading data into and retrieving data from the molecular database 102, maintains the integrity of the data stored in the molecular database 102, e.g., by implementing access control operations, and maintains the consistency of the data stored in the molecular database 102, e.g., by propagating modifications to molecules represented by molecule components. The operations of the molecular database management system 100 are described in more detail below with reference to FIG. 5-7.

Figure 2:
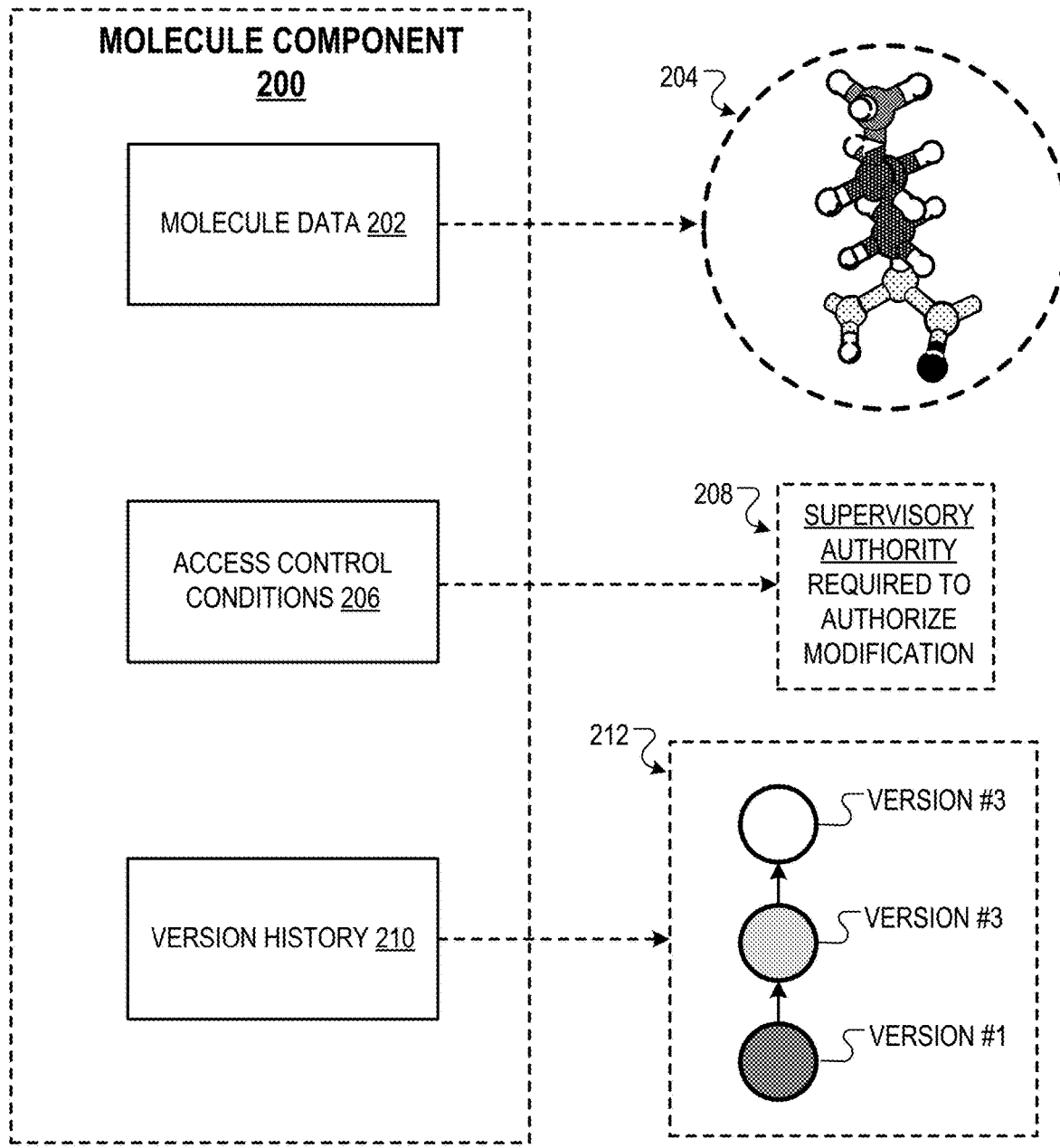
FIG. 2 provides an illustration of a molecule component.

FIG. 2 provides an illustration of a molecule component 200, e.g., stored in the molecular database described with reference to FIG. 1. The molecule component 200 includes molecule data 202 that defines a molecule 204, e.g., a DNA molecule, an RNA molecule, an XNA molecule, a protein molecule, a peptide molecule, an antibody molecule, a drug molecule, an antibody-drug conjugate molecule, a carbohydrate molecule, or a lipid molecule. Optionally, the molecule component 200 can include data defining one or more access control conditions 206, i.e., specifying conditions that must be satisfied in order for the molecule 204 to be modified. In the example illustrated in FIG. 2, the access control condition 208 specifies that modifying the molecule 204 requires "supervisory authority," e.g., of a user of the molecular database. Optionally, the molecule component 200 can include version history data 210 that identifies one or more previous versions 212 of the molecule, e.g., "version #1," "version #2," and "version #3.)

Figure 3:
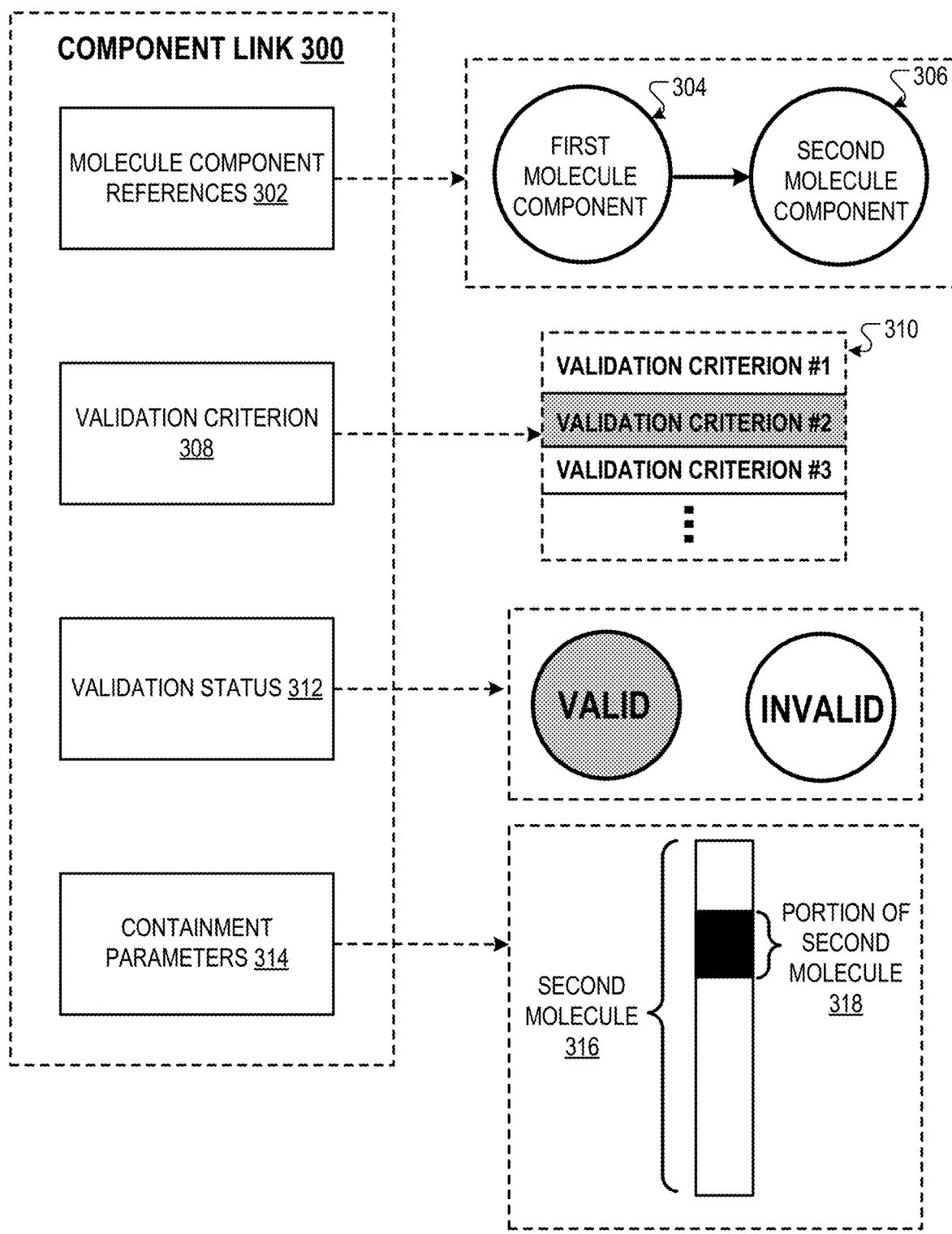
FIG. 3 provides an illustration of a component link.

FIG. 3 provides an illustration of a component link 300, e.g., stored in the molecular database described with reference to FIG. 1. The component link 300 includes molecule component references 302, i.e., that reference a pair of molecule components including a first molecule component 304 and a second molecule component 306. The molecule component references 302 can be represented, e.g., by an ordered tuple $(ID_1, ID_2)$, where $ID_1$ is a unique identifier of the first molecule component 304 and $ID_2$ is a unique identifier of the second molecule component 306.

The component link 300 is associated with a validation criterion 308 for evaluating whether the pair of molecule components referenced by the component link 300 have a valid containment relationship. The validation criterion 308 can be selected, e.g., by a user of the molecular database, e.g., from among a set of predefined validation criteria 310, e.g., "validation criterion #1," "validation criterion #2," etc. In some cases, the validation criterion 308 can define a sophisticated criterion for evaluating the validity of the containment relationship, e.g., a criterion that involves processing representations of the molecules corresponding to the pair of molecule components using a machine learning model, as will be described in more detail below.

The component link 300 includes a validation status 312, e.g., that defines whether the pair of molecule components referenced by the component link 300 have a valid containment relationship, i.e., as evaluated using the validation criterion 308.

The component link 300 can include containment parameters 314 that parameterize the evaluation of the validation criterion 308 of the component link 300. For instance, the validation criterion 308 can define that the first molecule component 304 (representing a first molecule) has a valid containment relationship with the second molecule component 306 (representing a second molecule 316) if the first molecule is included within a corresponding portion of the second molecule. In this instance, the containment parameters 314 can identify the corresponding portion 318 of the second molecule, i.e., with respect to which the containment relationship is evaluated. For example, the second molecule 316 can be defined by a sequence of bases, and the containment parameters can identify a subsequence of the sequence of bases defining the second molecule 316.

Figure 4:
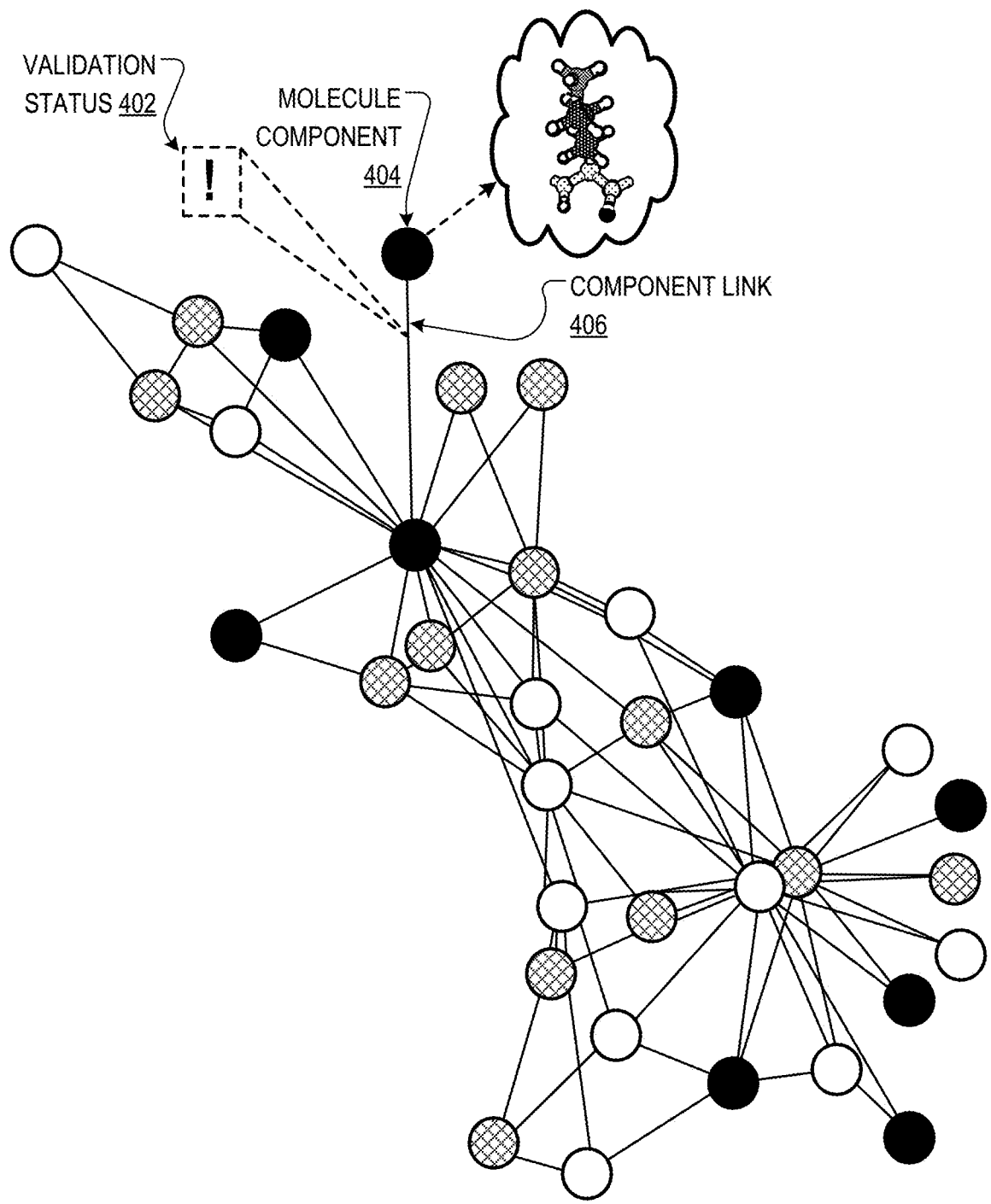
FIG. 4 provides an illustration of a molecular database.

FIG. 4 provides an illustration of a molecular database, where the circles represent molecule components (e.g., molecule component 404), the shading in a circle represents the type of molecule represented by the corresponding component link (e.g., DNA, RNA, protein, etc.), and the lines represent component links (e.g., component link 406). The validation status 402 of component link 406 is "invalid," which can be visually represented, e.g., to a user, by a "!" symbol (or in any other appropriate way).

Figure 5:
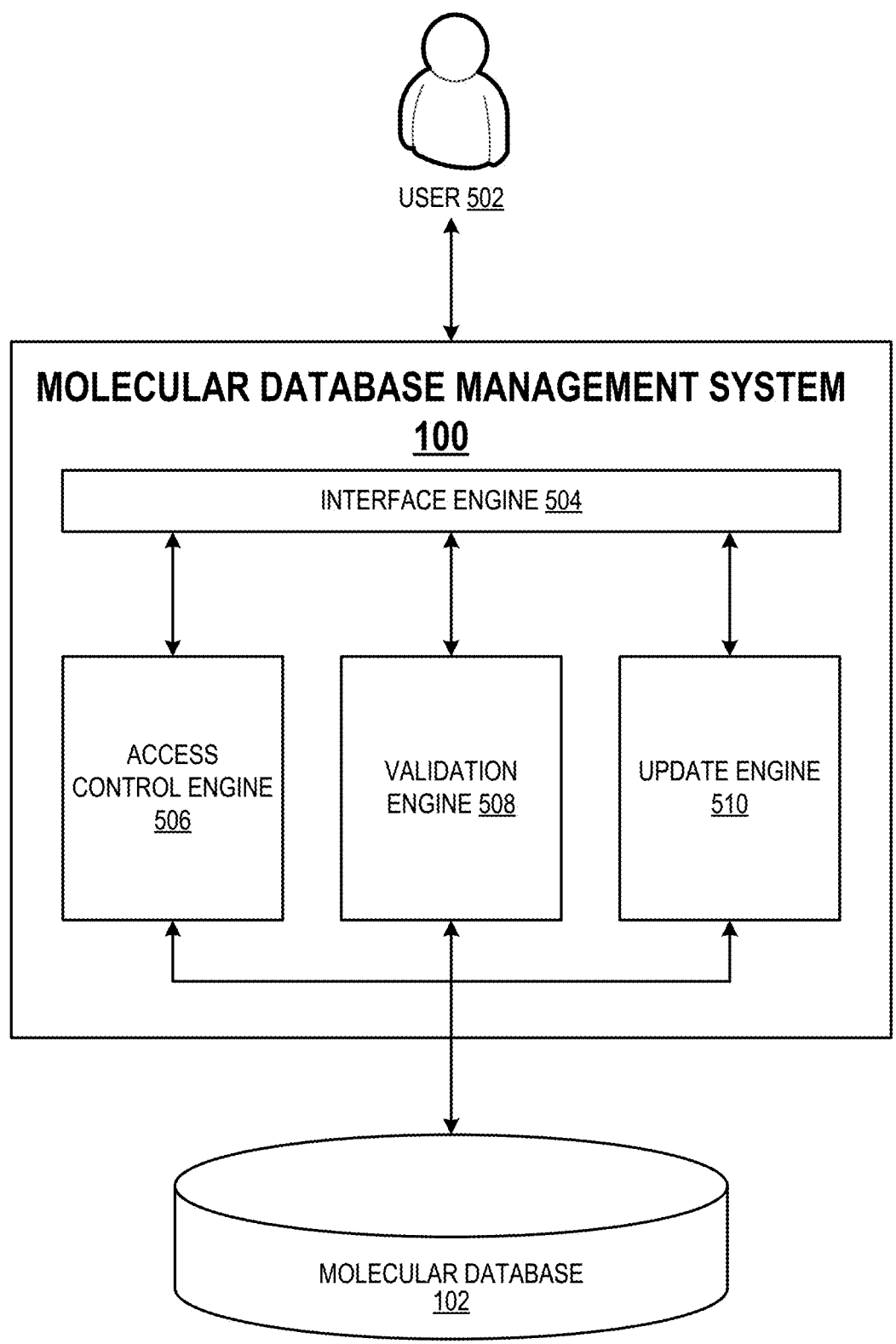
FIG. 5 shows an example molecular database management system.

FIG. 5 shows an example molecular database management system 100. The molecular database management system 100 is an example of a system implemented as computer programs on one or more computers in one or more locations in which the systems, components, and techniques described below are implemented.

The system 100 includes an access control engine 506, a validation engine 508, an update engine 510, and an interface engine 504, which are each described in more detail next.

The access control engine 506 is configured to receive a query comprising: (i) data identifying an action to be performed in the molecular database 102, e.g., to update a molecule component, and (ii) data identifying a user associated with the action, e.g., that requested the action. In response to receiving the query, the access control engine 506 determines whether the user is authorized to perform the action, e.g., based on access control conditions included in one or more molecule components that would be impacted by the action. Example techniques for determining whether a user is authorized to perform an action are described in more detail below with reference to FIG. 6.

The validation engine 508 is configured to receive a query identifying a component link, and in response to receiving the query, to determine a new validation status for the component link based on the molecules represented by the molecule components referenced by the component link. The validation engine 508 then updates the validation status of the component link to the new validation status. Example techniques for updating the validation status of a component link are described in more detail below with reference to FIG. 6.

The update engine 510 is configured to receive a request, e.g., from a user 502, to modify a molecule (referred to for convenience as a "target" molecule) represented by a molecule component (referred to for convenience as a "target" molecule component). The update engine 510 can modify the target molecule in accordance with the request, e.g., after querying the access control engine 506 to determine that the user 502 is authorized to modify the target molecule.

Updating the target molecule can affect the validity of containment relationships represented by component links that reference the target molecule component (referred to for convenience as "target" component links). In particular, updating the target molecule can cause containment relationships represented by one or more target component links to become invalid. For example, the target molecule component may be referenced by a target component link that describes the target molecule as being included in another molecule (referred to for convenience as a "related" molecule) represented by another molecule component (referred to for convenience as a "related" molecule component). In this example, updating the target molecule can cause the target component link to become invalid, i.e., because the updated target molecule may, in some cases, no longer be included in the related molecule. Therefore, after updating the target molecule, the update engine 510 can query the validation engine 508 to update the validation status for each target component link, i.e., that references the target molecule component.

In response to determining that the validation status of a target component link has become invalid, e.g., as a result of the modification to the target molecule, the update engine 510 can propagate the modification to the target molecule to restore the target component link to a valid state. More specifically, the update engine 510 can determine an update to: (i) the related molecule component referenced by the target component link, or (ii) the containment parameters of the target component link, or (iii) both, to restore the target component link to a valid state.

In some cases, propagating the modification to the target molecule can cause one or more other component links to become invalid. For example, propagating the modification to the target molecule can modify a related molecule represented by a related molecule component, which can in turn cause the respective validation states of one or more component links referencing the related molecule component to become invalid.

Therefore, the update engine 510 can iteratively repeat the operations described above to continue propagating the modifications to the target molecule through the molecular database 102. More specifically, each time the update engine 510 updates a molecule represented by a molecule component, the update engine 510 can determine whether the update caused any component links reference the molecule component to become invalid. In response to determining that the update to the molecule caused one or more component links that reference the molecule component to become invalid, the update engine 510 can further propagate the update to restore the validity of the affected component links.

Throughout the process of propagating modifications to a target molecule through the molecular database 102, prior to modifying a molecule component, the update engine 510 can query the access control engine 506 to determine whether the user 502 is authorized to modify the molecule component. (In this context, "the user" can refer to, e.g., the user that initiated the modifications being propagated by the update engine 510 through the molecular database 102). In response to determining that the user 502 is not authorized to modify the molecule component, and thus restore the validity of a component link referencing the molecule component, the update engine 510 can refrain from modifying the molecule component. Rather, the update engine 510 can notify the user 502, e.g., by way of the interface engine 504, or by email, or in any other appropriate manner, that the component link at issue has become invalid. Moreover, in some cases, the update engine 510 can be configured to request approval from the user 502 prior to updating certain molecule components, i.e., even if the access control condition for the molecule component authorizes the user to modify the molecule component.

Example processes for updating the validation statuses of target component links and propagating modifications through the molecular database 102 are described in more detail with reference to FIG. 6-7.

The interface engine 504 enables users 502 to provide inputs to the system 100, e.g., by way of a user interface (e.g., a graphical user interface, GUI) or an application programming interface (API) made available by the system 100. The interface engine 504 also enables the system 100 to make output data available to a user, e.g., by way of a user interface. A few examples of operations that can be enabled by the interface engine 504 are described next.

In some implementations, the interface engine 504 can enable a user 502 to query the molecular database 102. More specifically, the interface engine 504 can enable a user 502 to provide a query that identifies one or more selection criteria for selecting molecule components or component links from the molecular database 102. In one example, a user can query the molecular database 102 to request a listing of all component links in the molecular database with an invalid validation status. In response to receiving a user query by way of the interface engine 504, the system 100 can identify a set of molecule components or component links satisfying the selection criteria in the user query, and provide data identifying the set of molecule components or component links to the user 502.

In some implementations, the interface engine 504 can enable a user to request that the system 100 load molecular data defined in an external database into the molecular database 102. In response to the request, the system 100 can query the external database, e.g., by way of an API, to identify one or more molecules defined in the external database. The system 100 can then add a respective molecule component to the molecular database 102 corresponding to each of the molecules defined in the external database.

In some implementations, the interface engine 504 can enable a user to manually specify one or more molecules, and then request that the specified molecules be added to the molecular database 102. In response to the request, the system 100 can add a respective molecule component corresponding to each of the specified molecules to the molecular database.

In some implementations, the interface engine 504 can enable a user to request that the system 100 scan part or all of the molecular database 102 to identify possible component links that can be added to the molecular database 102. The user request can further specify a validation criterion for the possible component links. In response to the request, the system 100 can identify pairs of molecule components in the molecular database 102 that are not currently referenced by a component link associated with the specified validation criterion. The system 100 can evaluate, for each pair of molecule components, whether the specified validation criterion is satisfied by the pair of molecule components. The system 100 can then add a respective component link referencing each pair of molecule components that satisfies the specified validation criterion to the molecular database 102.

In some implementations, the interface engine 504 can enable a user to select a validation criterion for a component link in the molecular database 102, e.g., by enabling the user to select from a predefined list of validation criteria, or by enabling the user to manually define a custom validation criterion.

In some implementations, the interface engine 504 can enable a user to request that any component links with an invalid status be removed from the molecular database 102. In response to the request, the system 100 can scan the molecular database 102 to identify and remove any component links having an invalid status from the molecular database 102.

Figure 6:
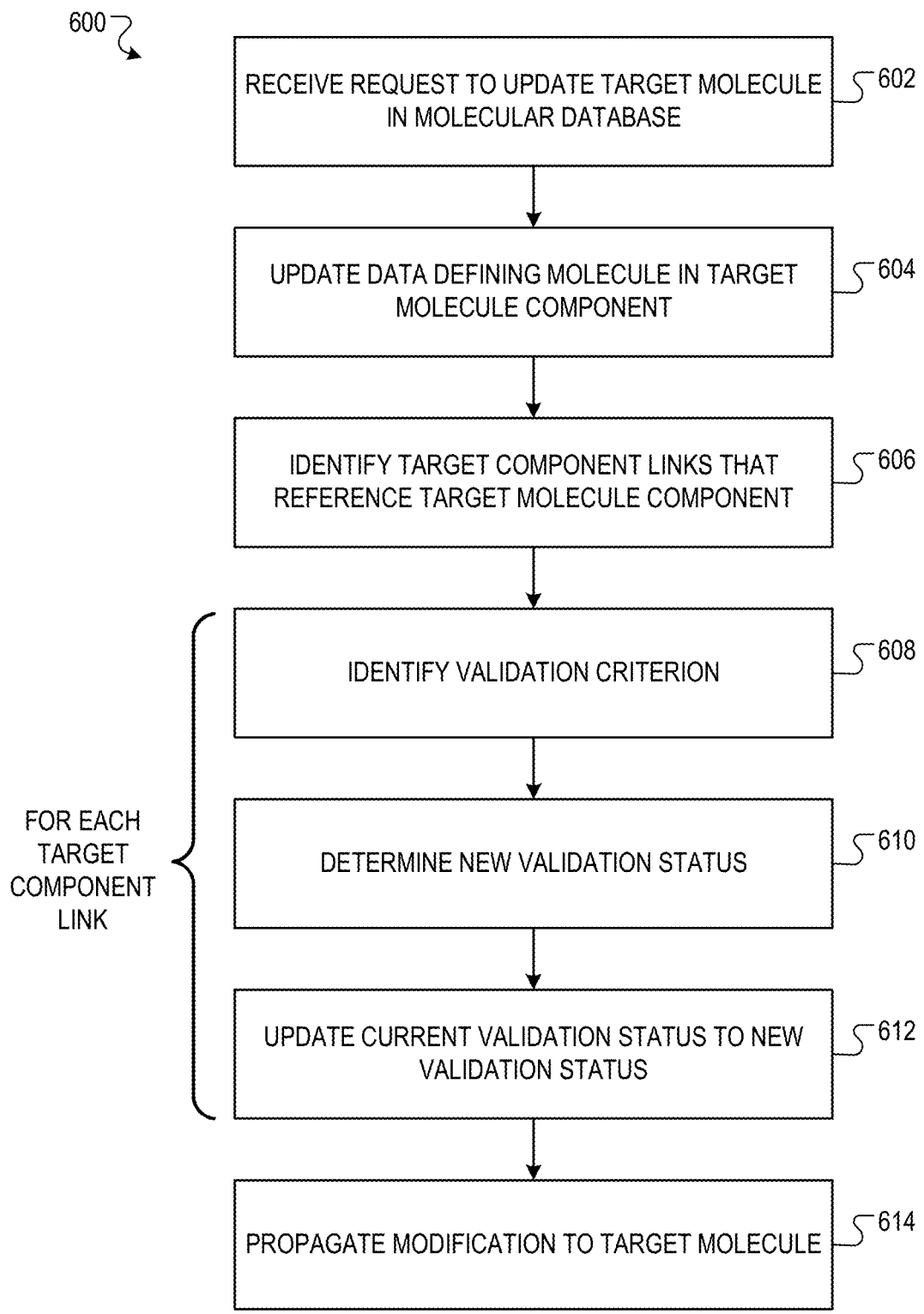
FIG. 6 is a flow diagram of an example process for modifying a target molecule represented by a target molecule component in a molecular database.

FIG. 6 is a flow diagram of an example process 600 for modifying a target molecule represented by a target molecule component in a molecular database. For convenience, the process 600 will be described as being performed by a system of one or more computers located in one or more locations. For example, a molecular database management system, e.g., the molecular database management system 100 of FIG. 1, appropriately programmed in accordance with this specification, can perform the process 600.

The system receives a request to update a target molecule represented by a target molecule component stored in a molecular database (602). The system can receive the request, e.g., from a user, by way of a user interface or an API. A user can specify a request to modify a molecule represented by a target molecule component using hierarchical editing language for macromolecules (HELM).

A user can request any appropriate modifications to a molecule. For instance, for a target molecule defined as a sequence of bases, a user can request that one or more of the bases in the sequence of bases defining the target molecule be deleted or updated to a different base. As another example, a user can request that one or more new bases be added at respective positions in the sequence of bases defining the target molecule. As another example, a user can request that the target molecule be replaced by a molecule included in the version history data for the target molecule component. That is, the user can request that the target molecule represented by the molecule component revert back to one of the molecules previously represented by the target molecule component.

In some cases, the system can receive a request to update a target molecule represented by a target molecule component as molecular data is imported into the molecular database from an external database, e.g., a legacy database. For example, the process of importing data into the molecular database can involve instantiating molecule components representing default molecules, and thereafter updating the molecule components by replacing the default molecules with molecules identified from the external database. It will be appreciated that the process of importing data into the molecular database can initially cause apparent inconsistencies in the molecular database as data is progressively loaded into the molecular database and default molecules are replaced by genuine molecules. (Moreover, inconsistencies may be present in the molecular data stored in the external database). The system can reflect these inconsistencies by temporarily transitioning component links into invalid states, before eventually reverting the component links back to valid states as the process of loading the data into the molecular database completes. In the absence of component links that can assume invalid states, the process of loading data into the molecular database could result in relationships between molecules being deleted, data being corrupted, and the like.

The system updates the data defining the target molecule represented by the target molecule component in accordance with the request (604). More specifically, prior to updating the target molecule, the system can determine whether the user is authorized to modify the target molecule based on the access control conditions for the target molecule component. If the system determines that the user does not have authorization to modify the target molecule component, the system can notify the user accordingly, e.g., by way of a user interface, and refrain from modifying the target molecule and terminate the process 600. If the system determines that the user has authorization to modify the target molecule, the system can modify the data defining the molecule represented by the target molecule component in accordance with the request. The system can also update the version history for the target molecule component, e.g., by augmenting the version history to include data defining the target molecule prior to the user modification.

The system can determine whether the user is authorized to modify the target molecule based on the access control conditions for the target molecule in any appropriate way. For example, the access control conditions for a target molecule component can define a listing of users that are designated as having authorization to modify the target molecule component. In this example, the system can determine that the user is authorized to modify the target molecule component only if the user is included in the listing of users that are designated as having authorization to modify the target molecule component.

The system identifies a set of target component links that reference the target molecule component (606). More specifically, the system identifies one or more target component links that each reference: (i) the target molecule component, and (ii) a respective related molecule component representing a related molecule. The system can identify the target component links, e.g., by filtering a list of the component links included in the molecular database to select only those component links that reference the target molecule component.

The system identifies, for each of the target component links, a respective validation criterion associated with the target component link (608). The validation criterion associated with a target component link defines a criterion for evaluating whether the pair of molecule components referenced by the target component link have a valid containment relationship.

The system determines, for each of the target component links, a new validation status for the target component link by evaluating the validation criterion associated with the target component link (610). A few examples of evaluating a validation criterion associated with a target component link are described next.

In one example, a validation criterion associated with a target component link can define that target molecule component has a valid containment relationship with a related molecule component if the target molecule is included within the related molecule. In this example, the system can evaluate the validation criterion by performing a comparison of a sequence of bases defining the target molecule with a corresponding subsequence of a sequence of bases defining the related molecule. (The location of the subsequence in the sequence of bases defining the related molecule can be defined, e.g., by one or more containment parameters of the target component link). In response to determining that the base at each position in the sequence of bases defining the target molecule matches the base at a corresponding position in the subsequence of the sequence of bases defining the related molecule, the system can determine that the validation criterion is satisfied. Otherwise, the system can determine that the validation criterion is not satisfied.

As another example, a validation criterion associated with a target component link can define that the target molecule component has a valid containment relationship with a related molecule component if a binding affinity between the target molecule and the related molecule satisfies a threshold. In this example, the system can evaluate the validation criterion by computing a binding affinity between the target molecule and the related molecule, and determining whether the binding affinity satisfies the threshold. The system can compute the binding affinity between the target molecule and the related molecule using any appropriate technique. For example, the system can process respective representations of the target molecule and the related molecule using a binding prediction machine learning model (e.g., implemented as a neural network) to generate the binding affinity.

The system updates the current validation status of each target component link to the new validation status for the target component link (612). In some cases, the system updates the validation status of a target component link from a "valid" status to an "invalid" status.

Optionally, the system can propagate the modifications to the target molecule to related molecules referenced by target component links that became invalid as a result of the modifications to the target molecule (614). Propagating the modifications to the target molecule can restore the validity of target component links that became invalid as a result of modifications to the target molecule. An example process for propagating the modifications to the target molecule is described in more detail with reference to FIG. 7.

Figure 7:
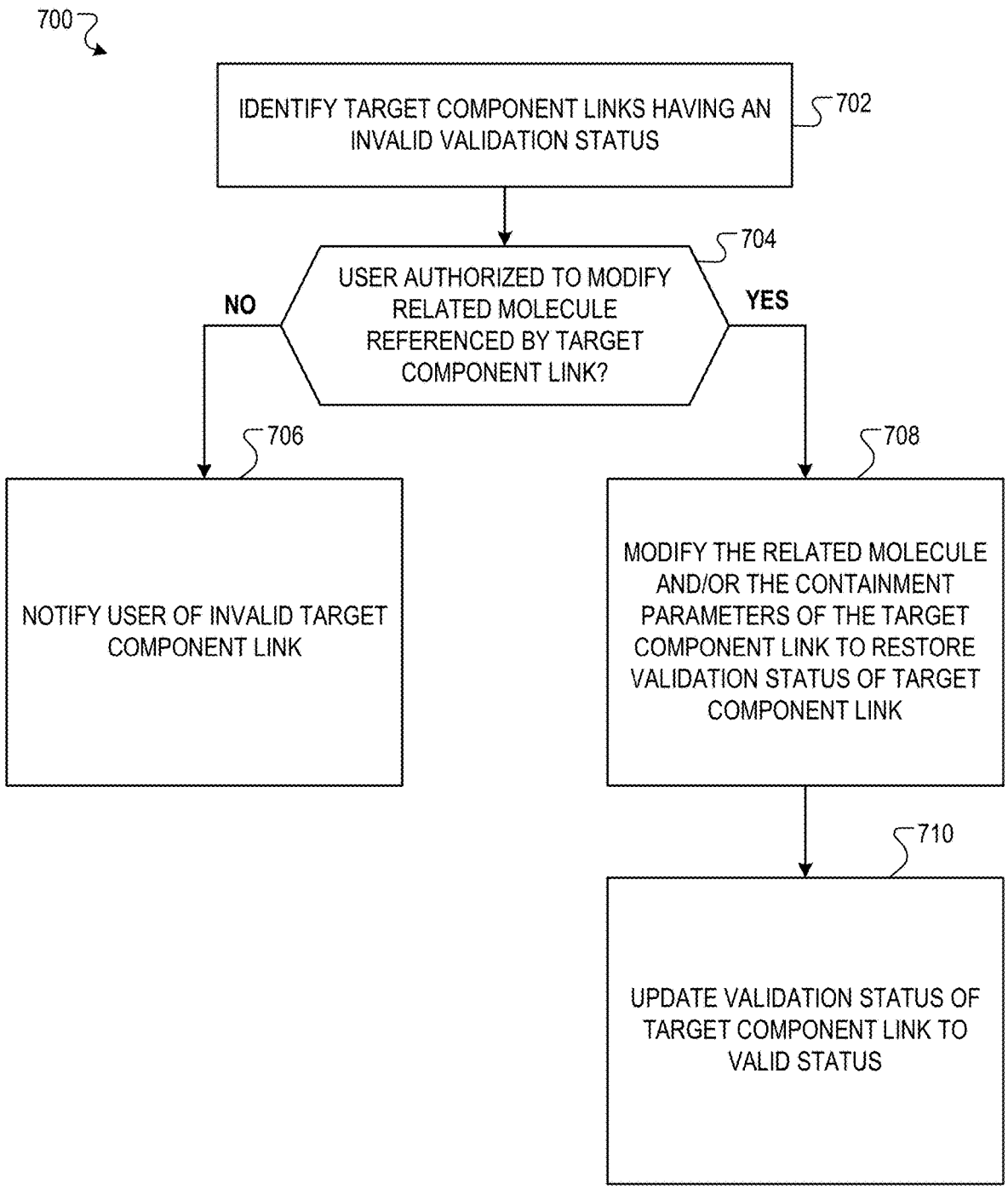
FIG. 7 is a flow diagram of an example process for propagating modifications to a target molecule in a molecular database.

FIG. 7 is a flow diagram of an example process 700 for propagating modifications to a target molecule in a molecular database. For convenience, the process 700 will be described as being performed by a system of one or more computers located in one or more locations. For example, a molecular database management system, e.g., the molecular database management system 100 of FIG. 1, appropriately programmed in accordance with this specification, can perform the process 700.

The system identifies each target component link that has an invalid validation status as a result of the modification to the target molecule (702).

The system determines, for each target component link having an invalid validation status, whether the user is authorized to modify the related molecule component referenced by the target component link (704). More specifically, the system can determine whether the user is authorized to modify a related molecule component based on access control conditions placed on the related molecule component. For instance, the system can determine whether the user satisfies the write access control conditions for the related molecule component.

In response to determining that the user is not authorized to modify a related molecule component referenced by a target component link having an invalid validation status, the system notifies the user of the invalid status of the target component link (706). For example, the system can notify the user of the invalid status of the target component link by way of a user interface, or by an email notification, or in any other appropriate manner. In some instances, the system may determine that the user does not satisfy either the write access control conditions or the read access control conditions for the related molecule component. In the instances, the system can refrain from notifying the user of the invalid status of the target component link, and rather notify another user that is designated as satisfying at least the read access control conditions for the related molecule component.

In response to determining that the user is authorized to modify a related molecule component referenced by a target component link having an invalid validation status, the system updates: (i) the related molecule, or (ii) the containment parameters of the target component link, or (iii) both, to restore the valid status of the target component link (708). A few examples of techniques for restoring the valid status of the target component link are described next.

In some cases, the target component link can have a validation criterion which defines that the target molecule component and the related molecule component have a valid containment relationship if the target molecule is included in a corresponding portion of related molecule. In these instances, the system can update the related molecule to include the target molecule, e.g., by replacing the corresponding portion of the related molecule with the target molecule. For example, the system can replace a subsequence of a sequence of bases defining the related molecule by a sequence of bases defining the target molecule.

In some cases, the target component link can have a validation criterion which defines that the target molecule component and the related molecule component have a valid containment relationship when a feature that jointly characterizes the target molecule and the related molecule satisfies a threshold. The feature can be, e.g., a similarity between sequences of bases defining the target molecule and the related molecule, or the binding affinity of the target molecule and the related molecule, or any other appropriate feature. In these cases, the system can perform a numerical optimization to determine an update to the related molecule or the containment parameters that causes the feature to satisfy the threshold. A few examples of numerical optimizations performed to determine an update to the related molecule or the containment parameters of the target component link are described next.

In one example, the target component link can have a validation criterion which defines that the target molecule component and the related molecule component have a valid containment relationship if a similarity measure between: (i) a sequence of bases defining the target molecule, and (ii) a subsequence of a sequence of bases defining the related molecule, satisfies a threshold. The containment parameters of the target component link can identify the subsequence of the sequence of bases defining the related molecule.

In this example, the system can perform a sequence alignment optimization to identify a new subsequence of the related molecule such that a similarity measure between the sequence of bases defining the target molecule and the new subsequence of the related molecule satisfies the threshold. The system can implement any appropriate sequence alignment optimization algorithm. An example of a sequence alignment optimization algorithm is described with reference to: Robert C. Edgar et al., "Multiple sequence alignment," *Current Opinion in Structural Biology*, Volume 16, Issue 3, June 2006, pp. 368-373. After performing the sequence alignment optimization, the system can replace the containment parameters of the target component link with new containment parameters identifying the position of the new subsequence of the sequence of bases defining the related molecule.

In some instances, as an alternative to or in combination with updating the containment parameters of the target component link, the system can update the related molecule based on the results of the sequence alignment optimization. More specifically, the system can use the results of the sequence alignment optimization to determine where a modification to the target molecule should be propagated into the related molecule. For example, if the target molecule is modified by inserting a base at a particular position in the sequence of bases of the target molecule, then sequence alignment can define a corresponding position in the sequence of bases of the related molecule. The system can update the related molecule by inserting the base in the corresponding position in the sequence of bases of the related molecule.

In another example, a target component link can have a validation criterion which defines that the target molecule component and the related molecule component have a valid containment relationship if a binding affinity between the target molecule and the related molecule satisfies a threshold. The system can perform an optimization to update the related molecule to cause the binding affinity between the related molecule and the target molecule to satisfy the threshold.

In this example, the system can measure binding affinity between the target molecule and the related molecule using a binding prediction machine learning model, as described above. The system can perform an optimization, e.g., using a black box optimization technique, to determine an updated version of the related molecule that, according to the binding prediction machine learning model, achieves a binding affinity with the target molecule that satisfies the threshold. Examples of black box optimization techniques are described with reference to: Daniel Golovin et al., "Google Vizier: a service for black-box optimization," *Proceedings of the 23$^{rd}$ ACM SIGKDD International Conference on Knowledge Discovery and Data Mining*, August 2017, pp. 1487-1495.

After restoring the valid status of the target component link, the system can update the validation status of the target component link from an "invalid" state to a "valid" state (710).

In some implementations, prior to modifying a related molecule component referenced by a target component link having an invalid validation status (e.g., at step 706), the system determines whether modifying the related molecule component will introduce new validation errors. For instance, the system can determine whether modifying the related molecule component would cause one or more component links referencing the related molecule component to become invalid. In response to determining that modifying the related molecule component will introduce new validation errors, the system can provide a user with options to: (i) cancel the modification of the related molecule component, or (ii) cancel the modification to the target molecule component. In response to determining that modifying the related molecule component will not introduce new validation errors, the system can provide a user with options to: (i) proceed with modifying the related molecule component, or (ii) cancel the modification to the related molecule component, or (iii) cancel the modification to the target molecule component.

This specification uses the term "configured" in connection with systems and computer program components. For a system of one or more computers to be configured to perform particular operations or actions means that the system has installed on it software, firmware, hardware, or a combination of them that in operation cause the system to perform the operations or actions. For one or more computer programs to be configured to perform particular operations or actions means that the one or more programs include instructions that, when executed by data processing apparatus, cause the apparatus to perform the operations or actions.

Embodiments of the subject matter and the functional operations described in this specification can be implemented in digital electronic circuitry, in tangibly-embodied computer software or firmware, in computer hardware, including the structures disclosed in this specification and their structural equivalents, or in combinations of one or more of them. Embodiments of the subject matter described in this specification can be implemented as one or more computer programs, i.e., one or more modules of computer program instructions encoded on a tangible non-transitory storage medium for execution by, or to control the operation of, data processing apparatus. The computer storage medium can be a machine-readable storage device, a machine-readable storage substrate, a random or serial access memory device, or a combination of one or more of them. Alternatively or in addition, the program instructions can be encoded on an artificially-generated propagated signal, e.g., a machine-generated electrical, optical, or electromagnetic signal, that is generated to encode information for transmission to suitable receiver apparatus for execution by a data processing apparatus.

The term "data processing apparatus" refers to data processing hardware and encompasses all kinds of apparatus, devices, and machines for processing data, including by way of example a programmable processor, a computer, or multiple processors or computers. The apparatus can also be, or further include, special purpose logic circuitry, e.g., an FPGA (field programmable gate array) or an ASIC (application-specific integrated circuit). The apparatus can optionally include, in addition to hardware, code that creates an execution environment for computer programs, e.g., code that constitutes processor firmware, a protocol stack, a database management system, an operating system, or a combination of one or more of them.

A computer program, which may also be referred to or described as a program, software, a software application, an app, a module, a software module, a script, or code, can be written in any form of programming language, including compiled or interpreted languages, or declarative or procedural languages; and it can be deployed in any form, including as a stand-alone program or as a module, component, subroutine, or other unit suitable for use in a computing environment. A program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub-programs, or portions of code. A computer program can be deployed to be executed on one computer or on multiple computers that are located at one site or distributed across multiple sites and interconnected by a data communication network.

In this specification the term "engine" is used broadly to refer to a software-based system, subsystem, or process that is programmed to perform one or more specific functions. Generally, an engine will be implemented as one or more software modules or components, installed on one or more computers in one or more locations. In some cases, one or more computers will be dedicated to a particular engine; in other cases, multiple engines can be installed and running on the same computer or computers.

The processes and logic flows described in this specification can be performed by one or more programmable computers executing one or more computer programs to perform functions by operating on input data and generating output. The processes and logic flows can also be performed by special purpose logic circuitry, e.g., an FPGA or an ASIC, or by a combination of special purpose logic circuitry and one or more programmed computers.

Computers suitable for the execution of a computer program can be based on general or special purpose microprocessors or both, or any other kind of central processing unit. Generally, a central processing unit will receive instructions and data from a read-only memory or a random access memory or both. The essential elements of a computer are a central processing unit for performing or executing instructions and one or more memory devices for storing instructions and data. The central processing unit and the memory can be supplemented by, or incorporated in, special purpose logic circuitry. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device, e.g., a universal serial bus (USB) flash drive, to name just a few.

Computer-readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's device in response to requests received from the web browser. Also, a computer can interact with a user by sending text messages or other forms of message to a personal device, e.g., a smartphone that is running a messaging application, and receiving responsive messages from the user in return.

Data processing apparatus for implementing machine learning models can also include, for example, special-purpose hardware accelerator units for processing common and compute-intensive parts of machine learning training or production, i.e., inference, workloads.

Machine learning models can be implemented and deployed using a machine learning framework, e.g., a TensorFlow framework.

Embodiments of the subject matter described in this specification can be implemented in a computing system that includes a back-end component, e.g., as a data server, or that includes a middleware component, e.g., an application server, or that includes a front-end component, e.g., a client computer having a graphical user interface, a web browser, or an app through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network (LAN) and a wide area network (WAN), e.g., the Internet.

The computing system can include clients and servers. A client and server are generally remote from each other and typically interact through a communication network. The relationship of client and server arises by virtue of computer programs running on the respective computers and having a client-server relationship to each other. In some embodiments, a server transmits data, e.g., an HTML page, to a user device, e.g., for purposes of displaying data to and receiving user input from a user interacting with the device, which acts as a client. Data generated at the user device, e.g., a result of the user interaction, can be received at the server from the device.

In addition to the embodiments described above, the following embodiments are also innovative:

Embodiment 1 is a method performed by one or more computers, the method comprising:
receiving a request to update a target molecule component stored in a molecular database, wherein:
the molecular database stores data defining: (i) a set of molecule components, and (ii) a set of component links;
each molecule component includes data defining a respective molecule; and
each component link includes data defining: (i) a pair of molecule components in the molecular database that are referenced by the component link, and (ii) a current validation status of the component link; and
in response to the request:
updating data defining a target molecule represented by the target molecule component;
identifying a set of target component links that reference the target molecule component;
identifying, for each of the target component links, a respective validation criterion associated with the target component link,
wherein a validation criterion associated with a target component link defines a criterion for evaluating whether the pair of molecule components referenced by the target component link have a valid containment relationship;
determining, for each of the target component links, a new validation status for the target component link by evaluating the validation criterion associated with the target component link; and
updating the current validation status of each target component link to the new validation status for the target component link.

Embodiment 2 is the method of embodiment 1, wherein for each of the target component links, the validation criterion associated with the target component link is specific to the target component link.

Embodiment 3 is the method of any one of embodiments 1-2, wherein for one or more of the target component links:
the target component link references: (i) the target molecule component representing the target molecule, and (ii) a related molecule component representing a related molecule; and
the validation criterion associated with the target component link defines that the target molecule component and the related molecule component have a valid containment relationship only if the target molecule is included in the related molecule.

Embodiment 4 is the method of any one of embodiments 1-3, wherein for one or more of the target component links:
the target component link references: (i) the target molecule component representing the target molecule, and (ii) a related molecule component representing a related molecule; and
the validation criterion associated with the target component link defines that the target molecule component and the related molecule component have a valid containment relationship only if a similarity measure between the target molecule and a corresponding portion of the related molecule satisfies a threshold.

Embodiment 5 is the method of embodiment 4, wherein the similarity measure between the target molecule and the corresponding portion of the related molecule measures a similarity between: (i) a sequence of bases defining the target molecule, and (ii) a subsequence of a sequence of bases defining the related molecule.

Embodiment 6 is the method of embodiment 5, wherein the similarity measure is based on a Hamming distance measure.

Embodiment 7 is the method of any one of embodiments 1-6, wherein for one or more of the target component links:
the target component link references: (i) the target molecule component representing the target molecule, and (ii) a related molecule component representing a related molecule; and
the validation criterion associated with the target component link defines that the target molecule component and the related molecule component have a valid containment relationship only if a binding affinity between the target molecule and the related molecule satisfies a threshold.

Embodiment 8 is the method of any one of embodiments 1-7, wherein each component link includes data defining a set of containment parameters that parameterize evaluation of the validation criterion associated with the component link.

Embodiment 9 is the method of embodiment 8, further comprising, for one or more of the target component links:
identifying that the new validation status for the target component link indicates an invalid status; and
updating: (i) a related molecule represented by a related molecule component referenced by the target component link, or (ii) containment parameters of the target component link, or (iii) both, to cause the target molecule component and the related molecule component to have a valid containment relationship.

Embodiment 10 is the method of embodiment 9, further comprising, prior to updating the related molecule represented by the related molecule component:
determining that an access control condition for the related molecule component authorizes modifications to the related molecule represented by the related molecule component.

Embodiment 11 is the method of embodiment 9, further comprising, after updating: (i) the related molecule, or (ii) containment parameters of the target component link, or (iii) both:
updating the current validation status of the target molecule component to indicate a valid status.

Embodiment 12 is the method of embodiment 9, wherein the validation criterion associated with the target component link defines that the target molecule component and the related molecule component have a valid containment relationship when a feature that jointly characterizes the target molecule and the related molecule satisfies a threshold; and
wherein updating: (i) the related molecule, or (ii) containment parameters of the target component link, or (iii) both, comprises:
performing a numerical optimization to determine updated versions of: (i) the related molecule, (ii) the containment parameters of the target component link, or (iii) both, that cause the feature to satisfy the threshold.

Embodiment 13 is the method of embodiment 12, wherein the feature that jointly characterizes the target molecule and the related molecule comprises a similarity measure between: (i) a sequence of bases defining the target molecule, and (ii) a corresponding subsequence of a sequence of bases defining the related molecule; and
wherein performing the numerical optimization comprises:

performing a sequence alignment optimization to align the sequence of bases defining the target molecule with a subsequence of a sequence of bases defining the related molecule;
wherein an updated version of the containment parameters of the target component link identify a position of the subsequence in the sequence of bases defining the related molecule.

Embodiment 14 is the method of embodiment 12, wherein the feature that jointly characterizes the target molecule and the related molecule comprises a binding affinity of the target molecule and the related molecule; and
wherein performing the numerical optimization comprises:
optimizing a representation of the related molecule to cause a binding affinity generated by processing respective representations of the related molecule and the target molecule using a binding prediction machine learning model to satisfy the threshold.

Embodiment 15 is the method of any one of embodiments 1-14, further comprising:
determining that the new validation status for a target component link indicates an invalid status; and
generating a notification that the new validation status for the target component link indicates the invalid status.

Embodiment 16 is the method of embodiment 15, wherein generating the notification that the new validation status for the target component link indicates the invalid status comprises:
transmitting an email notification to a user, wherein the email notification specifies that the new validation status for the target component link indicates the invalid status.

Embodiment 17 is the method of any one of embodiments 1-16, wherein receiving the request to update the target molecule comprises:
receiving a request to replace the target molecule by a previous version of the target molecule, wherein the previous version of the target molecule is represented in a version history included in the target molecule component.

Embodiment 18 is the method of any one of embodiments 1-17, wherein the molecular database stores molecule components representing one or more of: deoxyribonucleic acid (DNA) molecules, ribonucleic acid (RNA) molecules, xeno nucleic acid (XNA) molecules, protein molecules, peptide molecules, antibody molecules, drug molecules, antibody-drug conjugate molecules, carbohydrate molecules, or lipid molecules.

Embodiment 19 is a system comprising: one or more computers and one or more storage devices storing instructions that are operable, when executed by the one or more computers, to cause the one or more computers to perform the method of any one of embodiments 1 to 18.

Embodiment 20 is a computer storage medium encoded with a computer program, the program comprising instructions that are operable, when executed by data processing apparatus, to cause the data processing apparatus to perform the method of any one of embodiments 1 to 18.

While this specification contains many specific implementation details, these should not be construed as limitations on the scope of any invention or on the scope of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially be claimed as such, one or more features from a claimed combination can in some cases be excised from the combination, and the claimed combination may be directed to a subcombination or variation of a subcombination.

Similarly, while operations are depicted in the drawings and recited in the claims in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a single software product or packaged into multiple software products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In some cases, multitasking and parallel processing may be advantageous.

What is claimed is:

1. A method performed by one or more computers, the method comprising:
receiving a request to update a target molecule component stored in a molecular database, wherein:
the molecular database stores data defining: (i) a set of molecule components, and (ii) a set of component links;
each molecule component includes data defining a respective molecule; and
each component link includes data defining: (i) a pair of molecule components in the molecular database that are referenced by the component link, and (ii) a current validation status of the component link; and
in response to the request:
updating data defining a target molecule represented by the target molecule component;
identifying a set of target component links that reference the target molecule component;
identifying, for each of the target component links, a respective validation criterion associated with the target component link,
wherein a validation criterion associated with a target component link defines a criterion for evaluating whether the pair of molecule components referenced by the target component link have a valid containment relationship;
determining, for each of the target component links, a new validation status for the target component link by evaluating the validation criterion associated with the target component link; and
updating the current validation status of each target component link to the new validation status for the target component link.

2. The method of claim 1, wherein for each of the target component links, the validation criterion associated with the target component link is specific to the target component link.

3. The method of claim 1, wherein for one or more of the target component links:
the target component link references: (i) the target molecule component representing the target molecule, and (ii) a related molecule component representing a related molecule; and
the validation criterion associated with the target component link defines that the target molecule component and the related molecule component have a valid containment relationship only if the target molecule is included in the related molecule.

4. The method of claim 1, wherein for one or more of the target component links:
the target component link references: (i) the target molecule component representing the target molecule, and (ii) a related molecule component representing a related molecule; and
the validation criterion associated with the target component link defines that the target molecule component and the related molecule component have a valid containment relationship only if a similarity measure between the target molecule and a corresponding portion of the related molecule satisfies a threshold.

5. The method of claim 4, wherein the similarity measure between the target molecule and the corresponding portion of the related molecule measures a similarity between: (i) a sequence of bases defining the target molecule, and (ii) a subsequence of a sequence of bases defining the related molecule.

6. The method of claim 5, wherein the similarity measure is based on a Hamming distance measure.

7. The method of claim 1, wherein for one or more of the target component links:
the target component link references: (i) the target molecule component representing the target molecule, and (ii) a related molecule component representing a related molecule; and
the validation criterion associated with the target component link defines that the target molecule component and the related molecule component have a valid containment relationship only if a binding affinity between the target molecule and the related molecule satisfies a threshold.

8. The method of claim 1, wherein each component link includes data defining a set of containment parameters that parameterize evaluation of the validation criterion associated with the component link.

9. The method of claim 8, further comprising, for one or more of the target component links:
identifying that the new validation status for the target component link indicates an invalid status; and
updating: (i) a related molecule represented by a related molecule component referenced by the target component link, or (ii) containment parameters of the target component link, or (iii) both, to cause the target molecule component and the related molecule component to have a valid containment relationship.

10. The method of claim 9, further comprising, prior to updating the related molecule represented by the related molecule component:
determining that an access control condition for the related molecule component authorizes modifications to the related molecule represented by the related molecule component.

11. The method of claim 9, further comprising, after updating: (i) the related molecule, or (ii) containment parameters of the target component link, or (iii) both:
updating the current validation status of the target molecule component to indicate a valid status.

12. The method of claim 9, wherein the validation criterion associated with the target component link defines that the target molecule component and the related molecule component have a valid containment relationship when a feature that jointly characterizes the target molecule and the related molecule satisfies a threshold; and
wherein updating: (i) the related molecule, or (ii) containment parameters of the target component link, or (iii) both, comprises:
performing a numerical optimization to determine updated versions of: (i) the related molecule, (ii) the containment parameters of the target component link, or (iii) both, that cause the feature to satisfy the threshold.

13. The method of claim 12, wherein the feature that jointly characterizes the target molecule and the related molecule comprises a similarity measure between: (i) a sequence of bases defining the target molecule, and (ii) a corresponding subsequence of a sequence of bases defining the related molecule; and
wherein performing the numerical optimization comprises:
performing a sequence alignment optimization to align the sequence of bases defining the target molecule with a subsequence of a sequence of bases defining the related molecule;
wherein an updated version of the containment parameters of the target component link identify a position of the subsequence in the sequence of bases defining the related molecule.

14. The method of claim 12, wherein the feature that jointly characterizes the target molecule and the related molecule comprises a binding affinity of the target molecule and the related molecule; and
wherein performing the numerical optimization comprises:
optimizing a representation of the related molecule to cause a binding affinity generated by processing respective representations of the related molecule and the target molecule using a binding prediction machine learning model to satisfy the threshold.

15. The method of claim 1, further comprising:
determining that the new validation status for a target component link indicates an invalid status; and
generating a notification that the new validation status for the target component link indicates the invalid status.

16. The method of claim 15, wherein generating the notification that the new validation status for the target component link indicates the invalid status comprises:
transmitting an email notification to a user, wherein the email notification specifies that the new validation status for the target component link indicates the invalid status.

17. The method of claim 1, wherein receiving the request to update the target molecule comprises:
receiving a request to replace the target molecule by a previous version of the target molecule, wherein the previous version of the target molecule is represented in a version history included in the target molecule component.

18. The method of claim 1, wherein the molecular database stores molecule components representing one or more of: deoxyribonucleic acid (DNA) molecules, ribonucleic acid (RNA) molecules, xeno nucleic acid (XNA) molecules, protein molecules, peptide molecules, antibody molecules, drug molecules, antibody-drug conjugate molecules, carbohydrate molecules, or lipid molecules.

19. A system comprising:
one or more computers; and
one or more storage devices communicatively coupled to the one or more computers, wherein the one or more storage devices store instructions that, when executed by the one or more computers, cause the one or more computers to perform operations comprising:
receiving a request to update a target molecule component stored in a molecular database, wherein:
the molecular database stores data defining: (i) a set of molecule components, and (ii) a set of component links;
each molecule component includes data defining a respective molecule; and
each component link includes data defining: (i) a pair of molecule components in the molecular database that are referenced by the component link, and (ii) a current validation status of the component link; and
in response to the request:
updating data defining a target molecule represented by the target molecule component;
identifying a set of target component links that reference the target molecule component;
identifying, for each of the target component links, a respective validation criterion associated with the target component link,
wherein a validation criterion associated with a target component link defines a criterion for evaluating whether the pair of molecule components referenced by the target component link have a valid containment relationship;
determining, for each of the target component links, a new validation status for the target component link by evaluating the validation criterion associated with the target component link; and
updating the current validation status of each target component link to the new validation status for the target component link.

20. One or more non-transitory computer storage media storing instructions that when executed by one or more computers cause the one or more computers to perform operations comprising:
receiving a request to update a target molecule component stored in a molecular database, wherein:
the molecular database stores data defining: (i) a set of molecule components, and (ii) a set of component links;
each molecule component includes data defining a respective molecule; and
each component link includes data defining: (i) a pair of molecule components in the molecular database that are referenced by the component link, and (ii) a current validation status of the component link; and
in response to the request:
updating data defining a target molecule represented by the target molecule component;
identifying a set of target component links that reference the target molecule component;
identifying, for each of the target component links, a respective validation criterion associated with the target component link,
wherein a validation criterion associated with a target component link defines a criterion for evaluating whether the pair of molecule components referenced by the target component link have a valid containment relationship;
determining, for each of the target component links, a new validation status for the target component link by evaluating the validation criterion associated with the target component link; and
updating the current validation status of each target component link to the new validation status for the target component link.

* * * * *